(12) United States Patent
Jaroszeski et al.

(10) Patent No.: US 6,937,890 B2
(45) Date of Patent: Aug. 30, 2005

(54) NONPENETRATING ELECTROPORATION DEVICE

(75) Inventors: Mark J. Jaroszeski, Wesley Chapel, FL (US); Richard Gilbert, Tampa, FL (US); Richard Heller, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 59 days.

(21) Appl. No.: 09/772,561

(22) Filed: Jan. 30, 2001

(65) Prior Publication Data

US 2002/0042588 A1 Apr. 11, 2002

Related U.S. Application Data

(63) Continuation-in-part of application No. 09/213,218, filed on Dec. 17, 1998, now Pat. No. 6,314,316.
(60) Provisional application No. 60/215,255, filed on Jun. 30, 2000.

(51) Int. Cl.[7] .............................. A61N 1/30; C12M 1/42
(52) U.S. Cl. ....................................... 604/20; 435/285.2
(58) Field of Search ................ 607/115–118, 148–153; 604/19, 20; 435/173.6, 461, 285.2

(56) References Cited

U.S. PATENT DOCUMENTS

| | | |
|---|---|---|
| 1,099,062 A | 6/1914 | Laposkey |
| 4,970,154 A | 11/1990 | Chang |
| 5,318,514 A | 6/1994 | Hofmann |
| 5,439,440 A | 8/1995 | Hofmann |
| 5,674,267 A | 10/1997 | Mir et al. |
| 5,707,349 A | 1/1998 | Edwards |
| 5,869,326 A | 2/1999 | Hofmann |
| 5,873,849 A | 2/1999 | Bernard |
| 5,983,130 A | 11/1999 | Phipps et al. |
| 6,009,345 A | 12/1999 | Hofmann |

FOREIGN PATENT DOCUMENTS

| | | |
|---|---|---|
| WO | 96/39226 | 12/1996 |
| WO | 98/47562 | 10/1998 |

*Primary Examiner*—Michael J. Hayes
(74) *Attorney, Agent, or Firm*—Smith & Hopen, P.A.; Ronald E. Smith; Molly L. Sauter

(57) ABSTRACT

The manipulator includes a support and at least one member affixed to and extending away from the support. The member has at least two differentially activatable areas of conductivity. The members are configured to establish a first electromagnetic field in vivo between selected areas of conductivity sufficient to manipulate a molecule relative to a target tissue and to establish a second, typically higher, electromagnetic field sufficient to cause transient permeability of a cell membrane within the target tissue. Restraining means are also described for restricting movement of the members with relation to each other. One method of using the device is for enhancing the delivery of a molecule into a tissue site; another is for poration of the tissue alone or in combination with the migration. The target tissue may include a tumor, organ, or wound site.

5 Claims, 11 Drawing Sheets

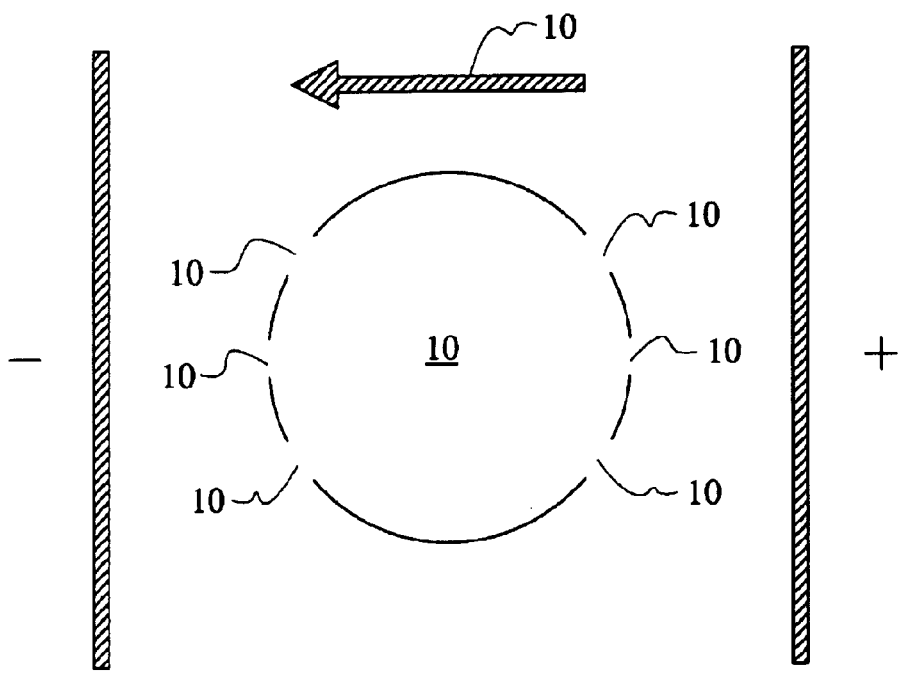
FIG. 1
Prior Art
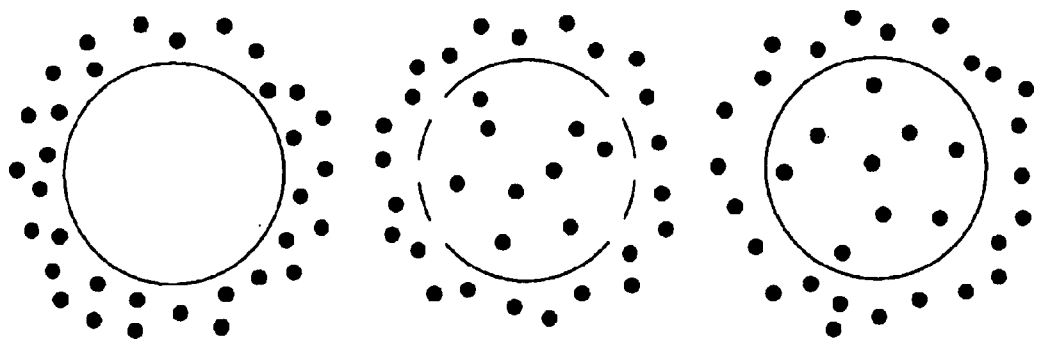
FIG. 2A
Prior Art
FIG. 2B
Prior Art
FIG. 2C
Prior Art

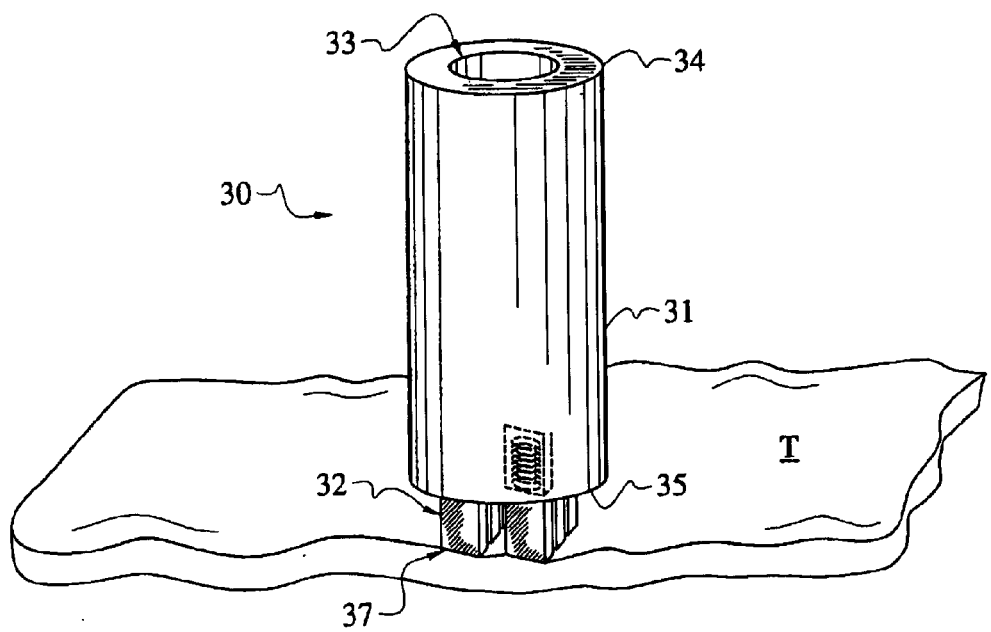
FIG. 5
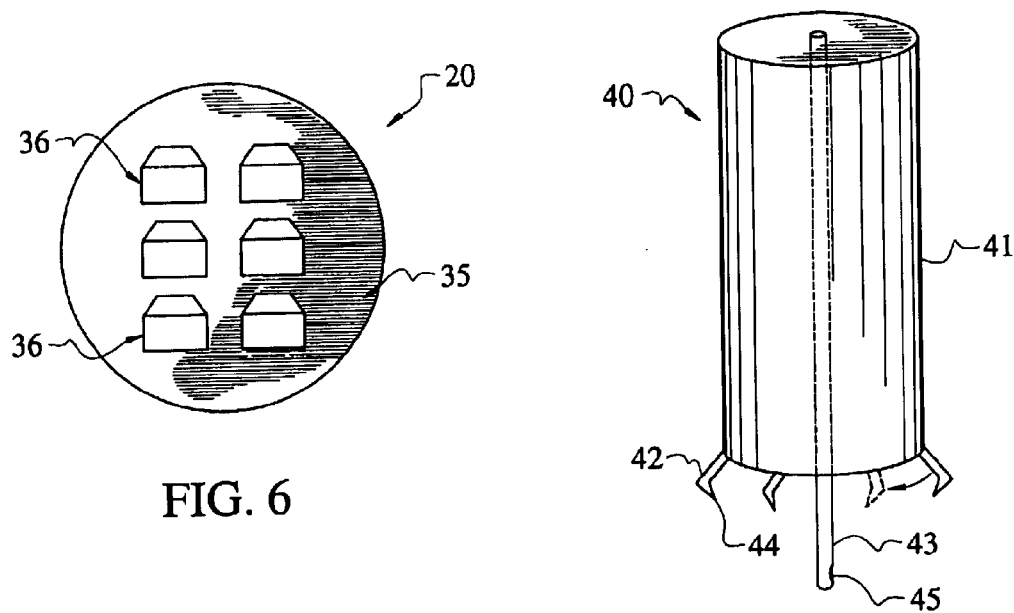
FIG. 6
FIG. 7

NONPENETRATING ELECTROPORATION DEVICE

CROSS-REFERENCE TO RELATED INVENTION

This application is a Continuation-In-Part of U.S. Utility Application, "Nonpenetrating Electroporation Device and Method," Ser. No. 09/213,218, filed Dec. 17,1998, now U.S. Pat. No. 6,314,316, and also claims priority to Ser. No. 60/215,255, filed Jun. 30, 2000, for "Nonpenetrating Electroporation Electrode and Method."

BACKGROUND OF THE INVENTION

1. Field of the Invention

The present invention related to methods and apparatus for delivering molecules into a target cell, and more particularly, to such methods and apparatus for achieving such delivery through electroporation.

2. Description of Related Art

The effect of electromagnetic fields on cell membranes has been studied since the 1960s. Early research focused on describing observations that an applied electric field can break down cell membranes in vitro. Throughout the 1970s the topic was more common in the literature and continued to focus on describing the phenomenon that resulted from brief exposure to intense electric fields as well as the entry of exogenous molecules to the cell interior as a result of membrane breakdown. Applications began to emerge along with a better understanding of the reversible nature of cell membrane breakdown in the 1980s.

Prior research led to the current understanding that exposure of cells to intense electric fields for brief periods of time temporarily destabilized membranes. This effect has been described as a dielectric breakdown due to an induced transmembrane potential, and was termed "electroporation," or "electropermeabilization," because it was observed that molecules that do not normally pass through the membrane gain intracellular access after the cells were treated with electric fields. The porated state was noted to be temporary. Typically, cells remain in a destabilized state on the order of minutes after electrical treatment ceases.

The physical nature of electroporation makes it universally applicable. A variety of procedures utilize this type of treatment, which gives temporary access to the cytosol. These include production on monoclonal proteins, and genetic transformation. In addition, dyes and fluorescent molecules have been used to investigate the phenomenon of electroporation. A notable example of loading molecules into cells in vivo is electrochemotherapy. The procedure utilizes a drug combined with electric pulses as a means for loading tumor cells with an anticancer drug, and has been performed in a number of animal models and in clinical trials by the present inventors. Also, plasmid DNA has been loaded into rat liver cells in vivo (Heller et al., *FEBS Lett.* 389, 225–28).

Protocols for the use of electroporation to load cells in vitro typically use a suspension of single cells or cells that are attached in a planar manner to a growth surface. In vivo electroporation is more complex because tissues are involved. Tissues are composed of individual cells that collectively make up a three-dimensional structure. In either case, the effects on the cell are the same. FIG. 1 illustrates details of the electroporation procedure. Electrodes and electrode arrays for delivering electrical waveforms for therapeutic benefit, including inducing electroporation, have been described by Bernard (WO 98/47562).

The loading of molecules by electroporation in vitro as well as in vivo is typically carried out by first exposing the cells or tissue of interest to a drug (FIG. 2). The cells or tissue are then exposed to electric fields by administering one or more direct current pulses. Electrical treatment is conducted in a manner that results in a temporary membrane destabilization with minimal cytotoxicity. The intensity of electrical treatment is described by the magnitude of the applied electric field. This field is defined as the voltage applied to the electrodes divided by the distance between the electrodes. Electric field strengths ranging from 1000 to 5000 V/cm have been used and are specific to the cells or tissue under investigation. Pulses are usually rectangular in shape; however, exponentially decaying pulses have also been used. The duration of each pulse is called pulse width. Molecule loading has been performed with pulse widths ranging from microseconds to milliseconds. The number of pulses delivered has ranged from one to eight. Typically, multiple pulses are utilized during electrical treatment.

For molecules to be delivered to the cell interior by electroporation, it is important that the molecule of interest be near the exterior of the cell membrane when a cell is in an electroporated state. It is also important to have molecules near substantially all cells within a treated tissue volume in order to provide efficient delivery to substantially all cells within the treatment volume.

Currently, molecules are injected systemically or directly into the treatment site. No attempt is made to produce a specific distribution. These methods do not ensure that the distribution of molecules is sufficient to provide effective delivery to substantially all the cells.

Electropermeabilization of tumor cell membranes has been reported (Rols et al., *Nature Biotechnology* 16,173, 1998) using applied electric pulses from surface electrodes in contact with the skin. Proteins and DNA can be transferred into the cells by incorporating either the protein or DNA carrying a reporter gene. The efficiencies of transfer for the protein and DNA were, respectively, 20% and 4%.

A first type of electrode known in the art comprises two parallel-plate electrodes placed on opposite sides of a tumor. Other electrodes known in the art at the present time comprise needles that are inserted into or around the tissue of interest. A third type comprises a planar arrangement of parallel wires that can be placed on the surface of the tissue.

Electrodes and methods known in the art do not provide molecular movement during the pre-electroporation time for electromigration, distribution, and post-electroporation time period when the cells are in a state of increased membrane permeability. The movement of molecules within the tissue is believed to affect an increase in the delivered quantity of molecules by enhancing movement into the cells.

SUMMARY OF THE INVENTION

It is therefore an object of the present invention to provide a device and method for manipulating molecules within a target tissue.

It is an additional object to provide such a device and method for manipulating molecules while a target cell is in a permeabilized state.

It is a further object to provide such a device and method that can provide a desired electromagnetic field distribution within a target tissue.

It is another object to provide such a device and method that can be configured to activate a multicomponent labile system at a desired site.

It is yet an additional object of the invention to provide a system for effecting tumor regression.

It is yet a further object of the invention to provide a system for effecting in vivo gene delivery via electroporation and electromigration.

It is another object of the invention to provide a system for effecting in vivo molecule delivery via electroporation.

It is yet a further object of the invention to provide a system for effecting in vivo molecule delivery via electromigration.

It is yet a further object of the invention to provide an electrode system for achieving electroporation within a target tissue.

It is also a further object of the invention to provide an electrode system that is adjustable for encompassing a wide variety of target tissue.

These object and others are attained by the present invention, a nonpenetrating electrode device for manipulating a molecule in vivo relative to a target tissue. The device comprises a support and at least two discrete electrodes extending away from and affixed to a support. Each electrode is connectable in circuit communication with a respective portion of a source of electrical energy.

The electrodes are movable between a first position wherein they are a first distance apart and a second position wherein they are a second distance apart. The first distance is greater than the second distance, and the electrodes are biased to the first distance. This movability is for positioning the electrodes in a desired relation to a selected portion of the target tissue.

Means are also provided for maintaining a desired distance between the electrodes. Specifically, the means are adapted to restrain the electrodes from extending to the first position.

The electrodes are adapted to deliver, for example, alternating current, direct current, pulsed alternating current, pulsed direct current, high- and low-voltage alternating current with variable frequency and amplitude, variable direct current waveforms, variable alternating current signals biased with variable direct current waveforms, and variable alternating current signals biased with constant direct current.

In addition, these objects and others are attained by the present invention, a device for manipulating a molecule in vivo relative to a target tissue. The device comprises a support and at least one member affixed to and extending away from the support. The member has at least two discrete electrodes, each electrode in circuit communication with a respective portion of a source of electrical energy and therefore being differentially activatable.

The discrete electrodes are configured to establish a first electromagnetic field in vivo between selected electrodes sufficient to manipulate a molecule relative to a target tissue. The electrodes are further configured to establish a second, typically higher, electromagnetic field sufficient to cause transient permeability of a cell membrane within the target tissue.

Several embodiments of the methods of the present invention include the use of a device as described above to enhance the delivery of a molecule such as a bioactive molecule, nucleic acid, amino acid, polypeptide, protein, antibody, glyoprotein, enzyme, oligonucleotide, plasmid DNA, chromosome, or drug, although this list is not intended to be exhaustive or limiting. In a related embodiment, the device may be used to cause the electromigration of a least two components of a multicomponent reactive system into opposition to permit a reaction to occur at a desired target tissue site. The target tissue may comprise a tumor, an organ, or a wound site.

The features that characterize the invention, both as to organization and method of operation, together with further objects and advantages thereof, will be better understood from the following description used in conjunction with the accompanying drawings. It is to be expressly understood that the drawings are for the purpose of illustration and description and are not intended as a definition of the limits of the invention. These and other objects attained, and advantages offered, by the present invention will become more fully apparent as the description that now follows is read in conjunction with the accompanying drawings.

BRIEF DESCRIPTION OF THE DRAWINGS

FIG. 1 (Prior Art) is a two-dimensional depiction of electroporation of a cell subjected to an electromagnetic field. Regions of membrane breakdown, depicted as pores, are formed at the ends of the cells facing the electrodes. Electromagnetic field exposure is achieved by applying a potential between electrodes − and +.

FIGS. 2A–2C (Prior Art) illustrate the process of delivering molecules by electroporation.

(FIG. 2A) A tumor cell in vitro or in vivo is exposed to the molecule of interest.

(FIG. 2B) Direct current pulses are administered to the cells to cause a temporary membrane destabilization that allows the molecules to more freely enter the cell interior.

(FIG. 2C) Cells return to their normal state after pulsation, leaving the drug within the cells.

FIG. 5 illustrates a second embodiment of a nonpenetrating molecule manipulator, including multiple electrodes disposed on downwardly depending posts from a generally cylindrical support.

FIG. 6 is a bottom plan view of the embodiment of FIG. 5.

FIG. 7 is a side view of a third embodiment of a nonpenetrating molecule manipulator, including inwardly moving electrode-support members.

DETAILED DESCRIPTION OF THE PREFERRED EMBODIMENTS

Figure 3:
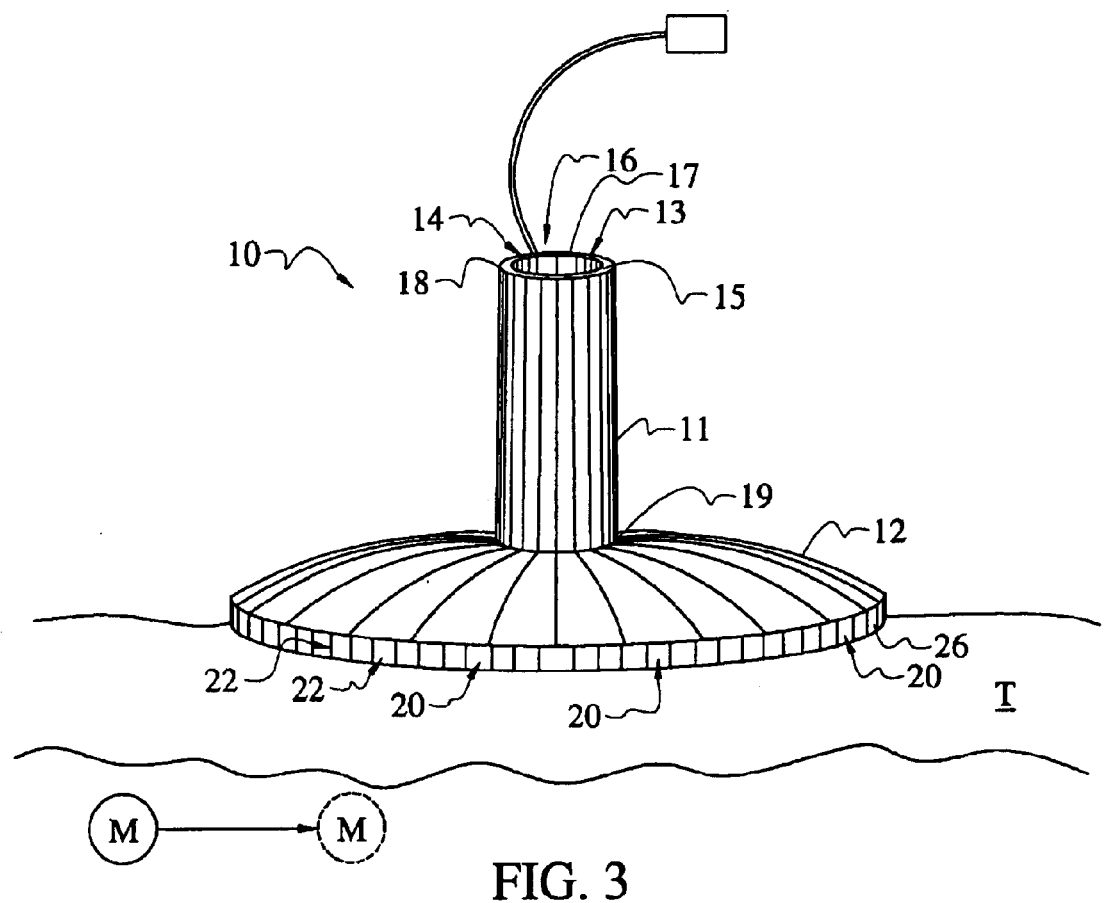
FIG. 3 illustrates a first embodiment of a nonpenetrating molecule manipulator, including an annular member having electrodes spaced apart by nonconductive material.
Figure 4:
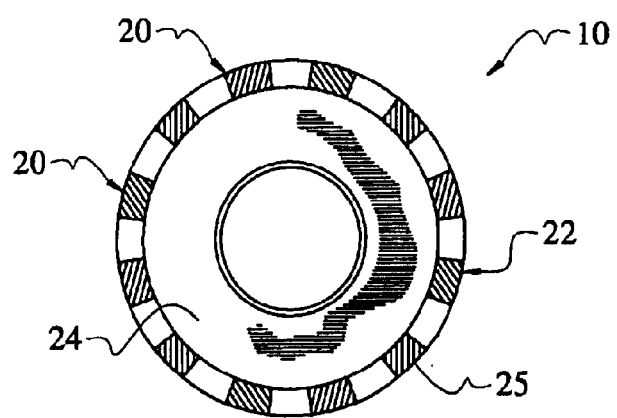
FIG. 4 is a bottom plan view of the embodiment of FIG. 3.
Figure 8:
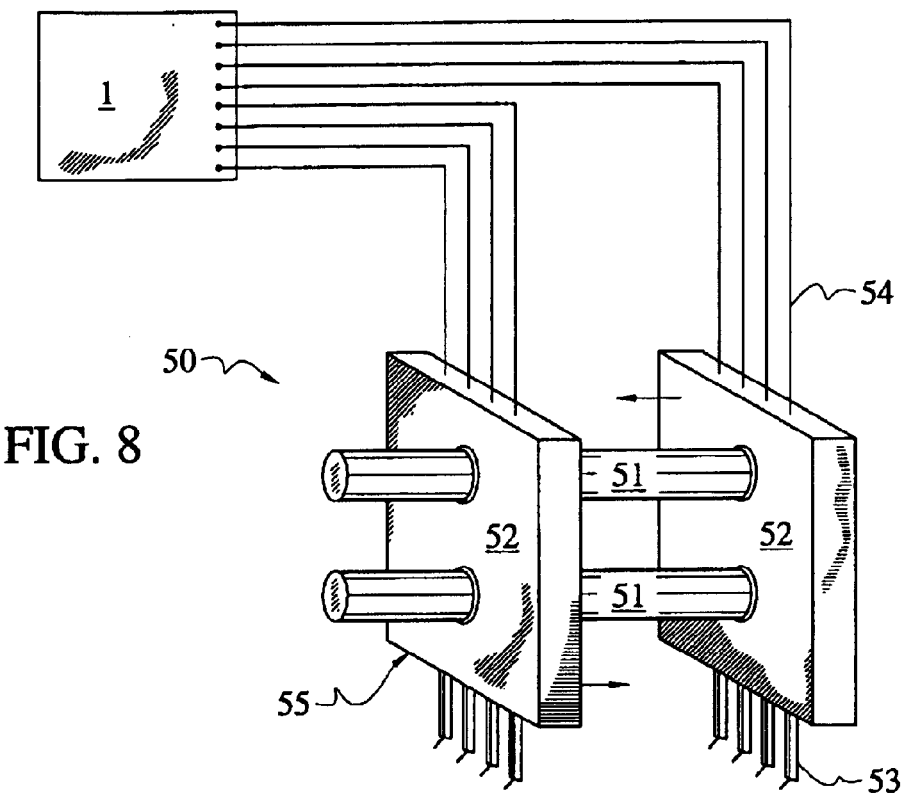
FIG. 8 is a side perspective view of a fourth embodiment of a nonpenetrating manipulator, including a pair of electrode-bearing members having an adjustable separation therebetween.

A description of the preferred embodiments of the present invention will now be presented with reference to FIGS. 3–23F.

A first embodiment of a nonpenetrating device 10 for manipulating a molecule M in vivo relative to a target tissue T (FIGS. 3 and 4) comprises a support that comprises a generally cylindrical post 11 having a portal 16 therethrough from a top end 18 to a bottom end 19.

A generally disc-like object 12 is affixed to the post's bottom end 19. The disc 12 has a bottom surface 24 with an outer downwardly depending annulus 25 that comprises alternating radial sectors of conductive 20 and nonconductive 22 areas. The conductive sectors 20 serve as the electrodes, and the nonconductive areas 22 serve to space the electrodes apart from each other. The annulus 25 is configured to surround a surface projection of a periphery of a least a portion of the target tissue T. In FIG. 3 the target tissue T is represented as the skin or surface of an organ, although this is not intended to be a limitation.

Preferably the disc 12 comprises a flexible material to permit shape adaptation with the selected portion of the target tissue. Also preferably the disc 12 has a transparent portion to permit visualization of the target tissue's selected portion therethrough.

An independent conductive lead 13 is in circuit communication with each of the conductive areas 22. Each lead 13 extends from the disc 12 through the post's portal 16 to the top end 18 thereof.

A plurality of contact means are positioned adjacent the post portal's top end 18 and in circuit communication with each lead 13. In a particular embodiment each contact means comprises a contact brush 14 that is affixed within the portal 16 against an inner wall 17 thereof. Interface means are positioned adjacent the post portal's top end 18 and has means for communicating with each contact brush 14 for establishing circuit communication with a signal generator 1. In a particular embodiment the interface means comprises a key interlock 15 that is insertable within the portal 16 at the top end 18. The key interlock 15 has a brush contact pad positioned for communication with each contact brush 14 in any of a plurality of manners well known in the art.

Each electrode 20 is in circuit communication with a respective portion of the source 1 of electrical energy. In a preferred embodiment this source comprises a pulse generator such as is known in the art (e.g., a PA-2000 or PA-4000, both from Cyto Pulse sciences, Inc., Columbia, Md.; a T820, BTX, Inc., San Diego, Calif.) and adapted to deliver pulses of a predetermined shape, voltage, duration, and separation. In particular, the source 1 should be adapted to deliver voltage to each electrode 20 for establishing a first, low-level and a second, typically higher-level electromagnetic field in vivo between selected electrodes. Selective control of the application of electrical signals between the individual electrodes can be accomplished in different ways, e.g., via the PA-201 Programmable Pulse Switch in combination with the PA-4000 generator (both from Cyto Pulse Sciences, Inc., Columbia, Md.), or it can be done manually, mechanically, or electrically. Based on the particular need of the application of the system, the electrical energy may include, but are not limited to, rectangular direct current pulses, exponentially decreasing DC pulses, alternating current, exponentially increasing DC pulses, bipolar DC pulses, DC biased DC waveforms, DC biased AC waveforms, pulsed alternating current, and radio frequency waves. The system may also be controlled by a computer system with the appropriate software designed to enable selective control of the signal generator as defined by the electrode, target tissue, and/or specific treatment.

The low-level field is for manipulating the molecule M relative to the target tissue T, here shown as a mass. The higher-level field is for causing transient permeability of a cell membrane within the target tissue T. Such a permeability is useful for permitting the molecule M to enter the interior of the cell (see FIGS. 1 and 2).

In use, the electrodes 20 are typically activated in opposing pairs, so that at least one electrode of each of a pair of electrodes 20 can be adapted to provide at least one pair of electrodes forming even pairs of opposite-polarity voltages approximately simultaneously in a 1+ to an opposite 1− relationship. Of course, other combinations can easily be envisioned by those of skill in the art. To illustrate, one of these combinations includes uneven pairs in odd numbered opposition; e.g., 2+ opposed to 1−, or 1+ opposed to 2−, and other numerical combinations. Further, it may be desired to selectively apply voltage to each electrode pair in a predetermined pattern. Such a means for imposing a preselected pattern may include, for example, a software program for driving a pulse generator to deliver signals to each selected electrode in the preselected pattern.

A second embodiment of a nonpenetrating device 30 for manipulating a molecule M in vivo relative to a target tissue T (FIGS. 5 and 6) comprises a generally cylindrical support 31 having a lumen 33 extending from a top end 34 through to a bottom end 35. A plurality of downwardly depending posts 32 are affixed adjacent the support's bottom end 35, with each post 32 having a conductive area 36 on a bottom surface 37 thereof. The posts 32 are disposed in spaced-apart relation from each other, and the conductive areas 36 comprise the electrodes.

In a particular embodiment, each post 32 is movably affixed to the support 31. Each post 32 is axially movable between a first position and a second position lower than the first position and is biased to the second position. This movement is for achieving contact between each post 32 and a target tissue T surface. In a specific type of movable post 32, as shown in FIG. 5, each post 32 is affixed to the support 31 in a spring-loaded fashion. Such movement permits a generally planar support bottom surface 35 to permit electrode contact with a nonplanar surface.

The lumen 33 may be used, for example, as a syringe guide to permit the introduction of the desired molecule into the tissue T through a syringe needle prior to activating the electrodes.

In FIG. 7 is shown a third embodiment 40 of a device similar to that 30 above. In this embodiment, the posts 42 have pointed conductive bottom tips 44 that are disposed at a radially inwardly facing angle to each other. Each post 42 is inwardly movable between a first position and a second position wherein the tips 44 are closer together than in the first position. The second position is for gripping tissue T between the tips 44. The pointed post shape illustrated here is not intended to be limiting; electrodes with other shapes may also be used this device as long as they are movable.

Another feature illustrated in this embodiment comprises a hollow needle 43 extending through the support 41. The needle 43, the tip of which extends beneath the posts 42, can carry a dose of the substance to be introduced via hole 45 into the tissue T or can be used as a portal through which the introduction can take place. In a related embodiment the needle 43 is movable axially to permit a selection of the depth of penetration.

A fourth embodiment 50 of the device (FIG. 8) includes a support 51 that movably holds a pair of insulating plates 52 in generally parallel fashion. In the embodiment shown the plates 52 comprise generally rectangular planar members. The support 51 includes means for altering the separation between the plates 52, which is useful for gripping tissue T therebetween.

Each plate 52 as a plurality of electrodes 53 affixed to its inward-facing surface 55, and leads 54 are connected to each electrode 53 for providing circuit communication with a signal generator 1.

A further embodiment of the present invention comprises a support and at least two discrete electrodes extending away from and affixed to the support in spaced-apart relation from each other. Each electrode is in circuit communication with a respective portion of a source of electrical energy adapted for delivering a pulse of predetermined duration and magnitude.

Another nonpenetrating device 10 for manipulating a molecule in vivo relative to a target tissue (FIGS. 10 and 11) comprises a support that includes a generally cylindrical handle member 60 having a channel 61 dimensioned for passing leads 62–65 therethrough, extending from a proximal end 66 to a distal end 67. The handle 60 comprises insulation from the leads 62–65 to permit safe handling by a user. Other shapes of the handle may be used as desired and known to one of ordinary skill in the art.

A plurality of electrodes, here four electrodes 68–71, are affixed at their proximal ends 72–75 to the handle's distal end 67 and are in electrical communication with respective leads 62–65. It will be understood by one of skill in the art that any number of electrodes two or greater may be employed, depending upon the size and configuration of the target tissue, and that the four disclosed here are merely exemplary. The leads 62–65 extend to connectors 76–79 at distal ends thereof that are adapted for electrical communication with a signal generator 1. The electrodes 68–71 are configured to encompass at least a portion of the target tissue T in a "pinching"-type arrangement (see FIG. 16).

Figure 12:
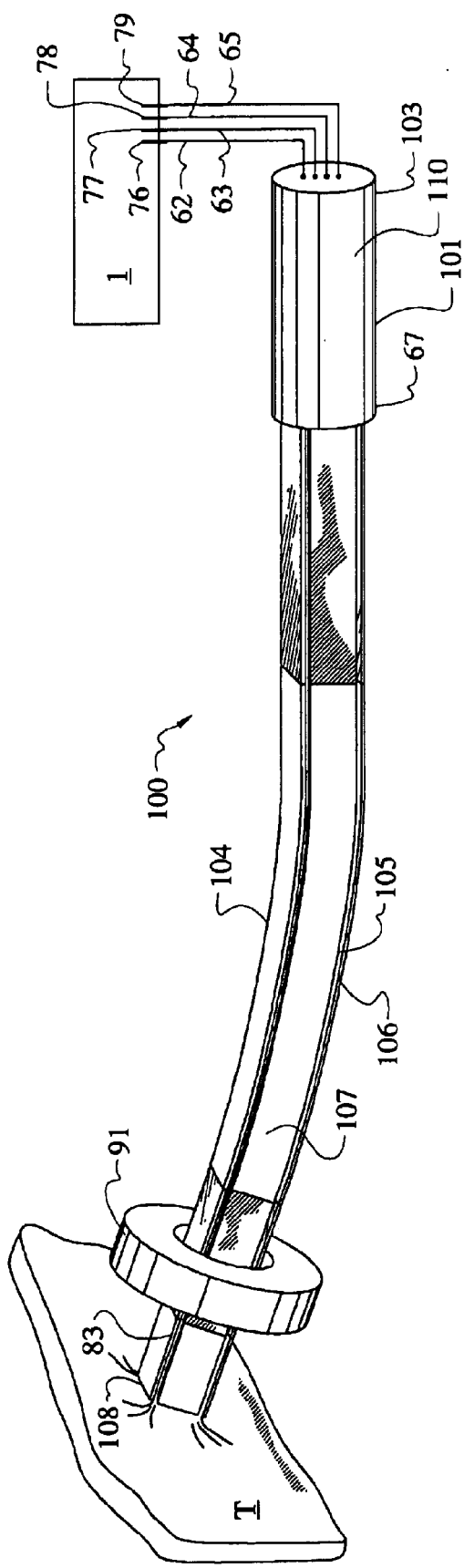
FIG. 12 is a side perspective view of an alternate embodiment of the nonpenetrating device having curved electrodes with barbed distal ends.

Details of the electrodes 68–71 in this embodiment will be presented for electrode 68, with the understanding that the other electrodes 69–71 have a similar configuration. (In FIG. 15, the electrode 69 is shown only partially to provide an inner view of electrode insulation 75.) Preferably the electrodes 68–71 comprise generally rectangular, elongated striplike members having insulation 140–143 extending from the proximal end 84. This insulation electrically isolates each electrode member and can extend all the way from the proximal end 84 all the way to the distal end 80, leaving only enough electrode surface exposed to allow energy transfer from the electrode members to the target tissue T. This insulation may be a separate member, a surface coating applied to the actual electrode member, or other type of insulation as known to those of skill in the art. At the distal end 80, the electrode 68 comprises a distal portion 80 that is electrically exposed at least on the side 82 facing the other electrodes to permit delivering a pulse therefrom. In a preferred embodiment the facing side 82 is substantially planar, although this geometry may be altered to suit a desired target tissue T. For example, in FIG. 12 is illustrated an alternate embodiment 100, wherein the electrodes 104–107 are curved to facilitate tissue contact. In addition, this embodiment shows the addition of barbs 108 to the distal ends 80 of the electrodes that serve as gripping means with respect to the target tissue T. These barbs are not limited to use solely in this embodiment, it is understood that this feature may be incorporated into any of the electrodes disclosed herein.

Figure 10:
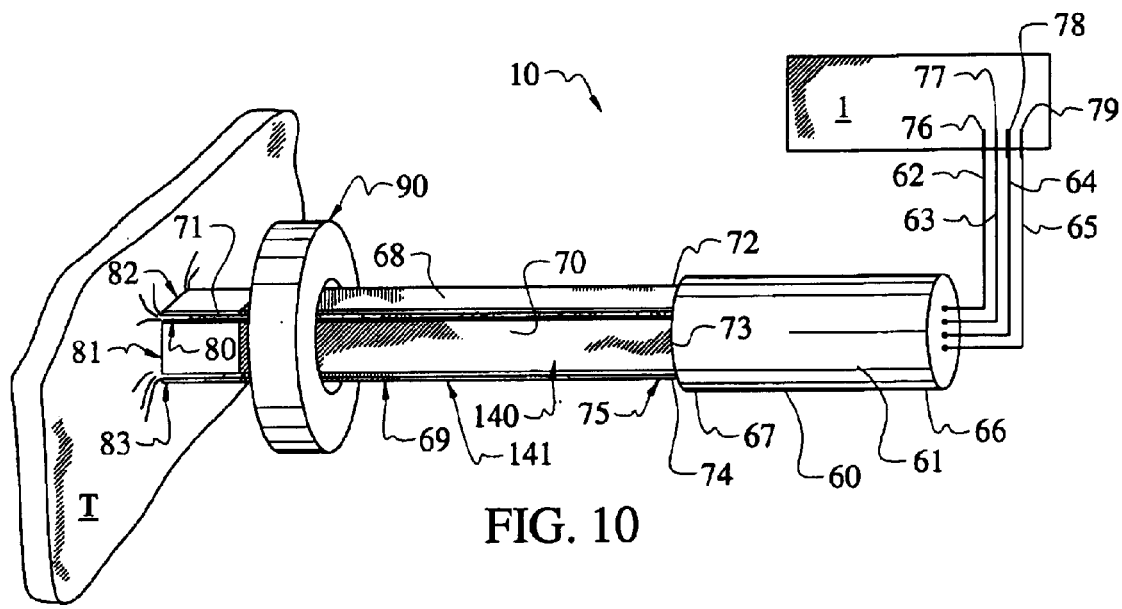
FIG. 10 is a side perspective view of a nonpenetrating electrode device of a further embodiment in the first position.
Figure 11:
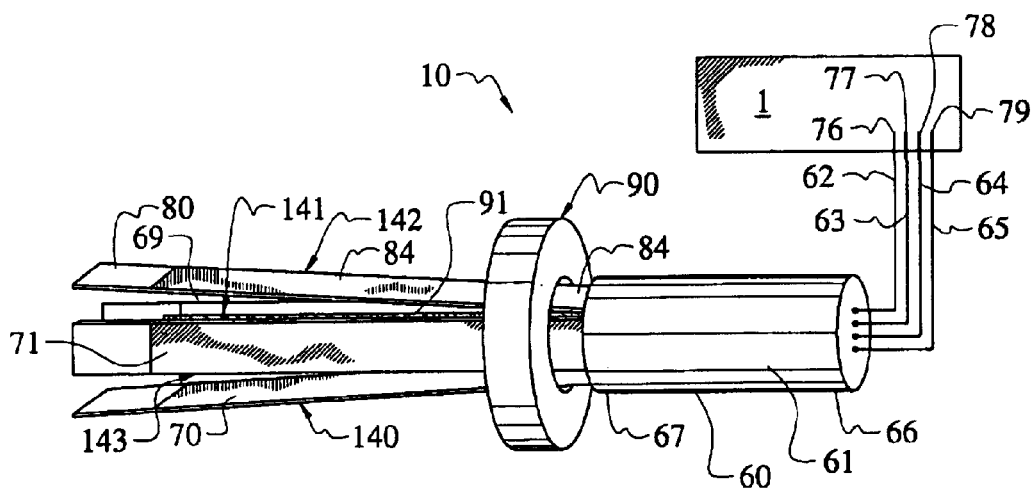
FIG. 11 is a side perspective view of the nonpenetrating electrode device of FIG. 10 in a second position.

In FIG. 11, the electrodes 68–71 are biased to the second position, wherein they are splayed apart at their distal ends. The electrodes 68–71 have sufficient flexibility to permit their being pressed together toward a first position (FIG. 11) adjacent the electrodes' proximal ends 84 and a second position (FIG. 10) adjacent the distal ends 80.

A second restraining means is also provided in a particular embodiment for restricting the minimum or maximum distances between the electrodes 68–71. In the embodiment shown in FIG. 11, the restraining means comprises a generally cylindrical insert 91 positionable in the lumen between the electrodes 68–71 that physically prevents the electrodes from approaching each other more closely than a desired distance. Again, any suitable shape for this device may be employed by one of ordinary skill in the art. As shown, this device can be used in combination with other electrode positioning means such as the torodial ring 90 or a set screw 123.

Figure 17:
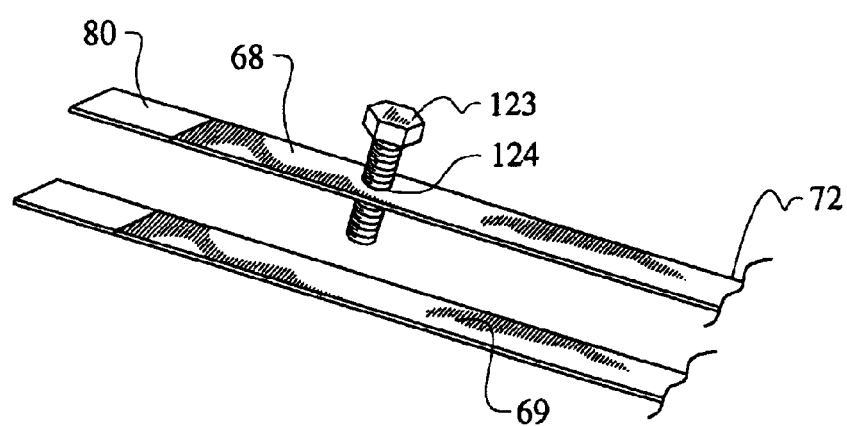
FIG. 17 is a bottom side perspective view of the electrode tips and a limiting screw showing one embodiment of an electrode spacing device.

This further device for selecting electrode spatial distances is shown in FIG. 17. The limiting means in the form of a set screw 123 passes through a bore 124 in the first electrode 68, extending from the outer to the inner face positioned in spaced relation between the proximal end 72 and distal end 80. The screw 123 is passed through the electrode 68 until its distal end 125 touches the inner face of the second electrode 69 and sets a predetermined minimum separation distance.

The leads 62–65 are in circuit communication with a respective portion of the source 1 of electrical energy as described before. In particular, the source 1 should be adapted to deliver voltage to each electrode 68–72 for establishing a first, low-level, and a second, typically high-level, electromagnetic field in vivo between selected electrodes. The low-level field is for manipulating the molecule relative to the target tissue T. The higher-level field is for causing transient permeability of a cell membrane with the target tissue T. Such a permeability is useful for permitting the molecule to enter the interior of the cell (see FIGS. 1 and 2).

Figure 13:
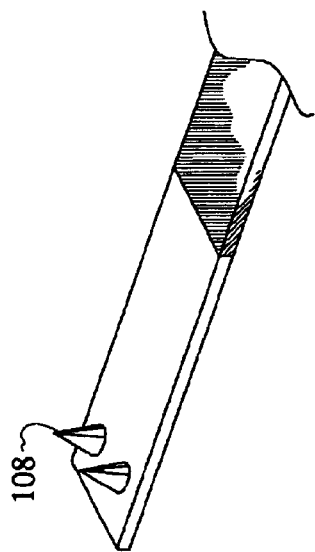
FIG. 13 is a close-up view of the distal end of the electrode member of FIG. 12, showing the barbs for gripping the target tissue.
Figure 14:
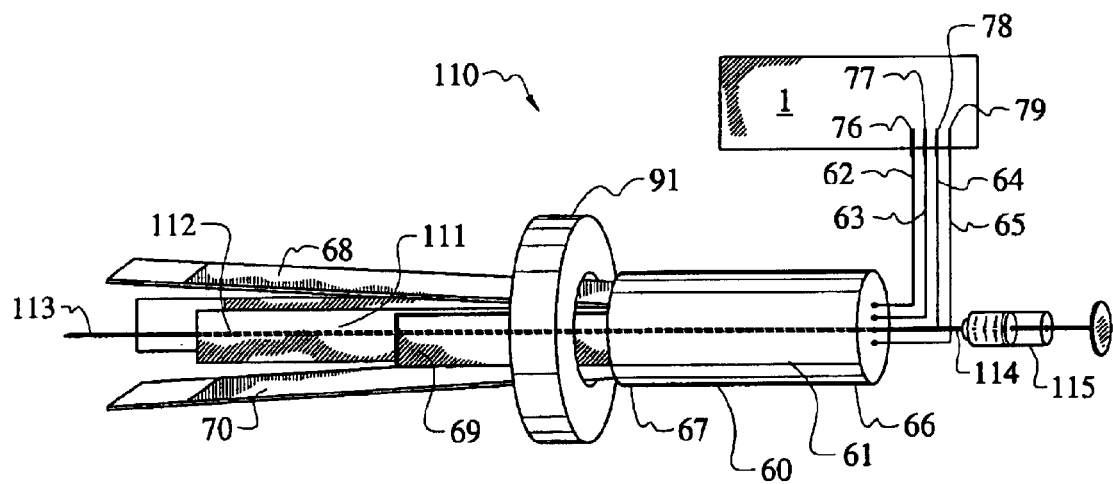
FIG. 14 is a side perspective view of another embodiment having a needle extending through the limiting insert.
Figure 15:
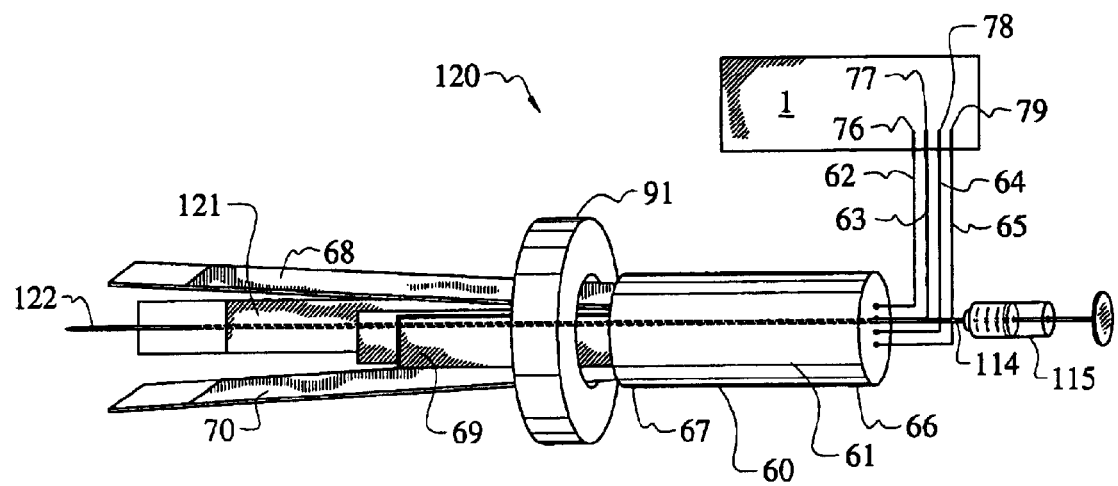
FIG. 15 is a side perspective view of a further embodiment having a needle extending along the inside of an electrode.
Figure 16:
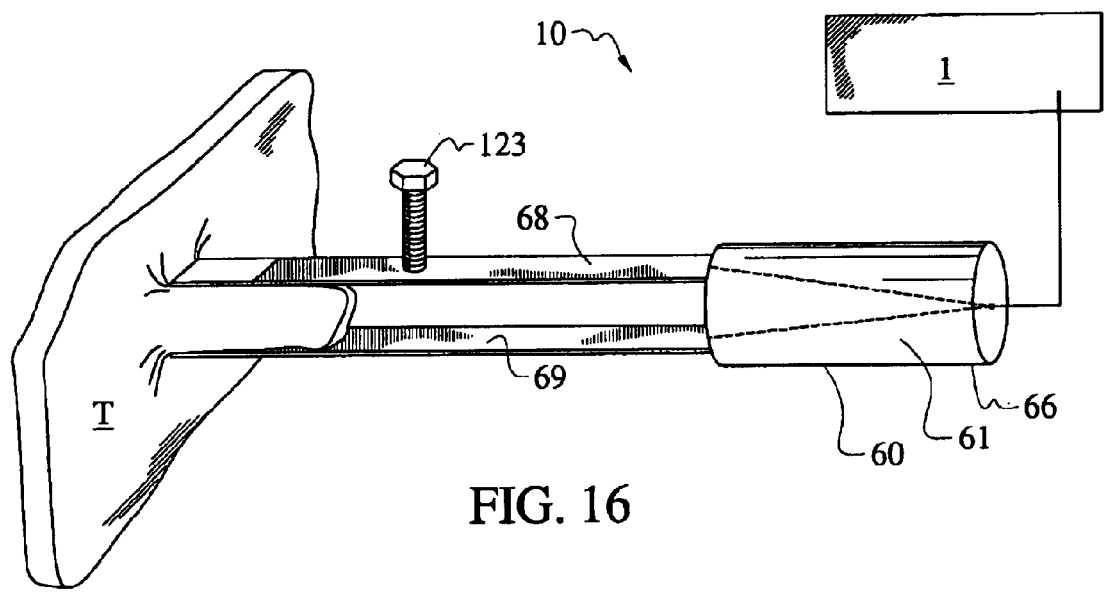
FIG. 16 is a side perspective view of a nonpenetrating electrode device in a "pinching"-type relationship with the target tissue.

A further embodiment 100, is shown in FIG. 13, the electrodes 104–107 may also comprise means for gripping tissue, such as barbs 108 at the distal ends 84. Additionally, other tissue attachment means may be used either alone or in combination; these including, but not limited to, bioadhesives, other adhesives, other chemical means or surface roughening on the electrode surfaces per se. Other chemical means may also include electrically conductive gels to facilitate the conduction of the energy to the target tissue.

In another embodiment, 110 (FIG. 14, electrode 69 being broken away), the insert 111 has a bore 112 therethrough. The device 110 further comprises a needle 113 extendable through the bore 112 and slidable relative to the electrodes 68–71. Another needle 114 is adapted for injecting a desired substance, for example, from a syringe 115, into the tissue at a desired target area for electroporation.

In yet another embodiment 120 (FIG. 15, electrode 69 and the insert 111 are shown broken away), at least one of the electrodes 121 has a needle 122 passing therealong and attached thereto, as shown, or alternately therethrough, again for injecting a desired substance into the tissue.

Figure 18:
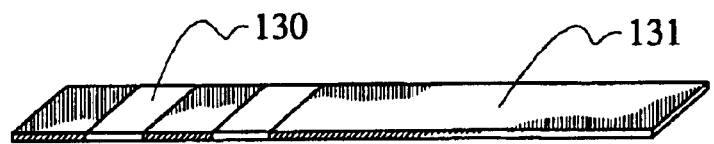
FIG. 18 is a side perspective view of another type of electrode member having discrete conductive and nonconductive portions contained in a single member.
Figure 19:
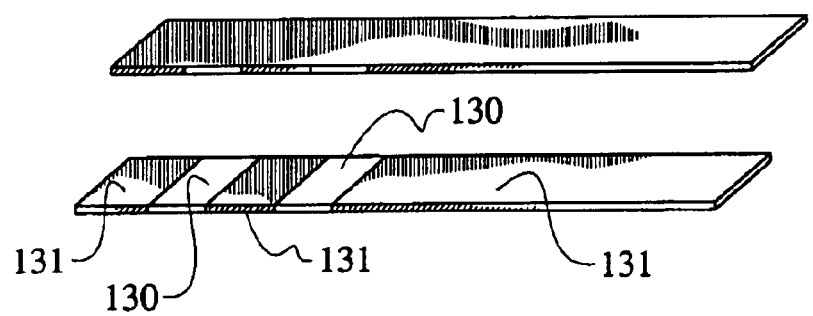
FIG. 19 is a side perspective view showing use of a plurality of electrode members that can be incorporated into a nonpenetrating electrode device.
Figure 20:
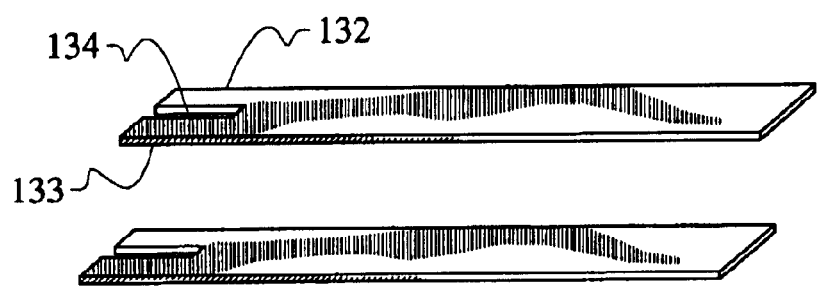
FIG. 20 is a further embodiment of the multiple independent conductive and nonconductive electrode showing another arrangement of the tissue contacting portions of the electrode member.
Figure 21:
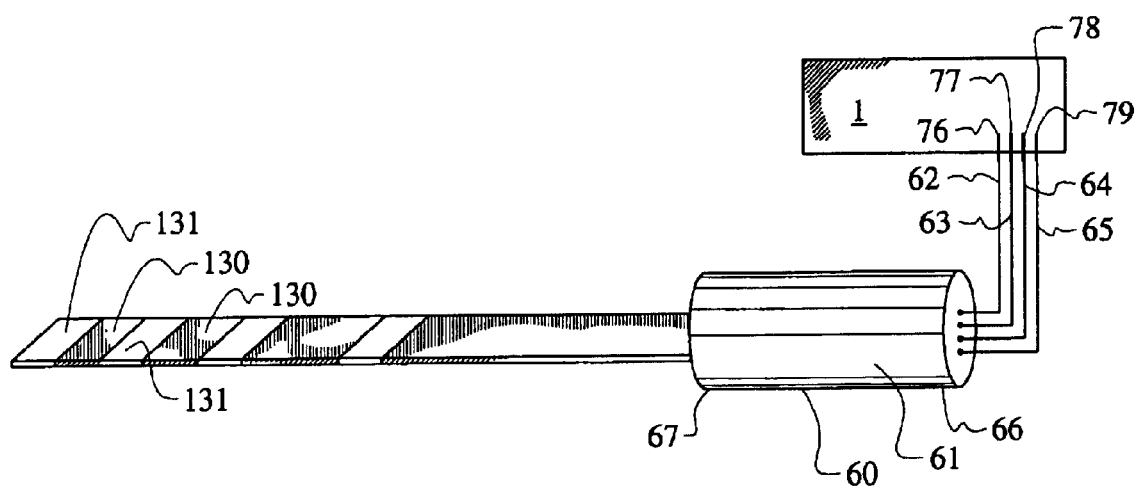
FIG. 21 illustrates a nonpenetrating electrode device using the electrode of FIG. 17.
Figure 22:
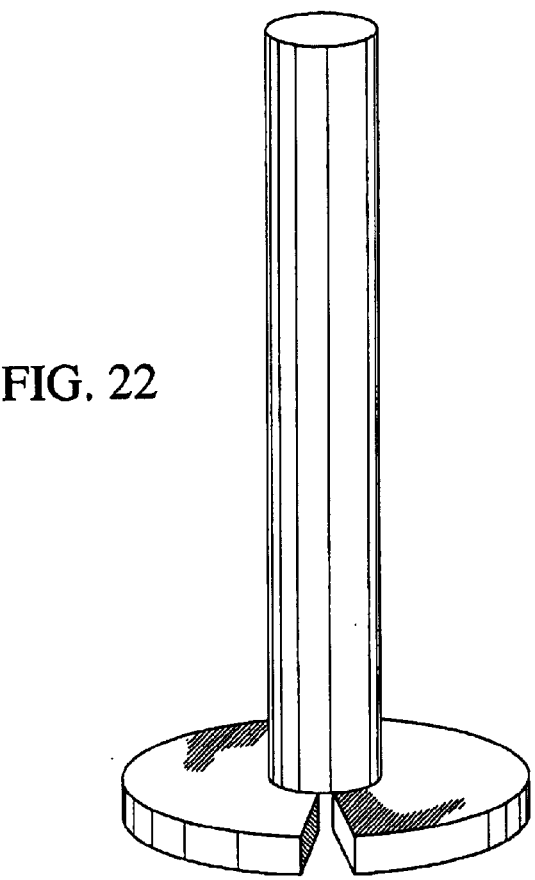
FIG. 22 is a side perspective view of a further embodiment of the tissue contacting portion of the electrode member, having a potion thereof removed to produce a cut-out, noncontinuous tissue-contacting surface.
Figure 23A:
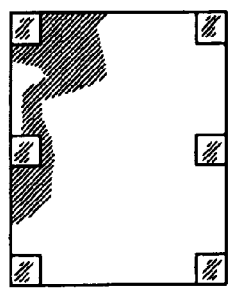
FIGS. 23A–23F illustrate additional embodiments of electrode contact members having alternate geometries for making tissue contact.
Figure 23D:
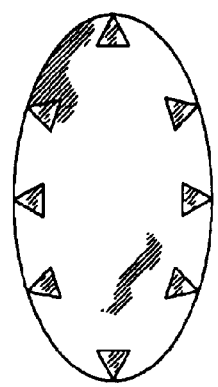
Figure 23B:
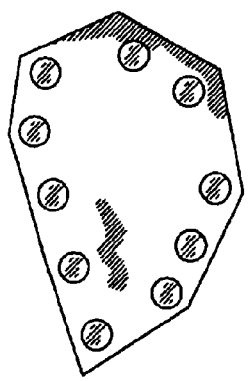
Figure 23E:
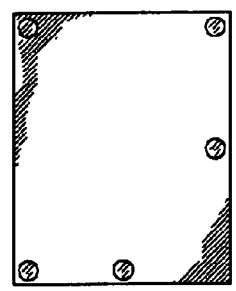
Figure 23C:
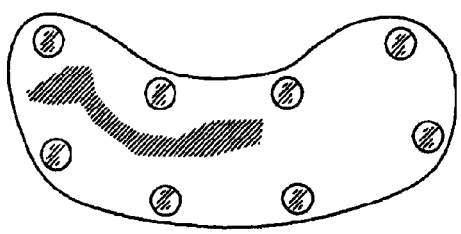
Figure 23F:
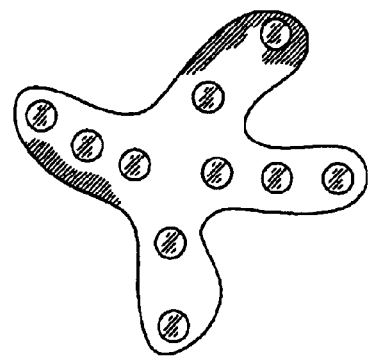

Another electrode member is shown in FIGS. 18–20. In this embodiment, the electrode comprises a single support member having discrete conductive and nonconductive portions contained along the length thereof. This electrode structure enables the device (FIG. 21) to be used either on the surface of the target tissue, in the lumen of an organ or other orifice, and also can be inserted into tissue that has become accessible by other means such as in surgery. This electrode has alternating areas of conductivity and these areas can be either one single + and − or comprise a plurality of alternating conductive areas along the single supporting member. Additionally, as shown in FIG. 19, the electrode device may comprise a plurality of the plural conductivity member electrodes. In use, the multiple electrode members may also be separated by a separation means to limit the distances between the members, as described earlier (see FIGS. 10 and 15).

A further electrode structure is shown in FIG. 20. In this embodiment, the distal conductive distal ends 132 and 133 are nonindependently addressable conductive regions of polarity and have an insulation portion 134 therebetween. That insulation portion 134 may comprise air, in the case of a cut-out portion, or a layer of physical insulation material.

Further examples of tissue-contacting portions of the electrode structures are shown in FIGS. 22 and 23A–F. In these embodiments, the tissue contact member is able to be noncontiguous (FIG. 22) as opposed to the member shown in FIG. 9. Alternative geometries for the contact members are also within the scope of the invention (FIGS. 23A–F), and these can be square, rectangular, elliptical, triangular, kidney-shaped, free-form, or any other shape configured to the needs of the system as defined by the target tissue. The various electrode members may also have alternate shapes and sizes as shown by items 140–142. The shapes of the various electrodes are exemplary only and are not intended to be limited, but any shape is useable as available to one of ordinary skill in the art.

Figure 9:
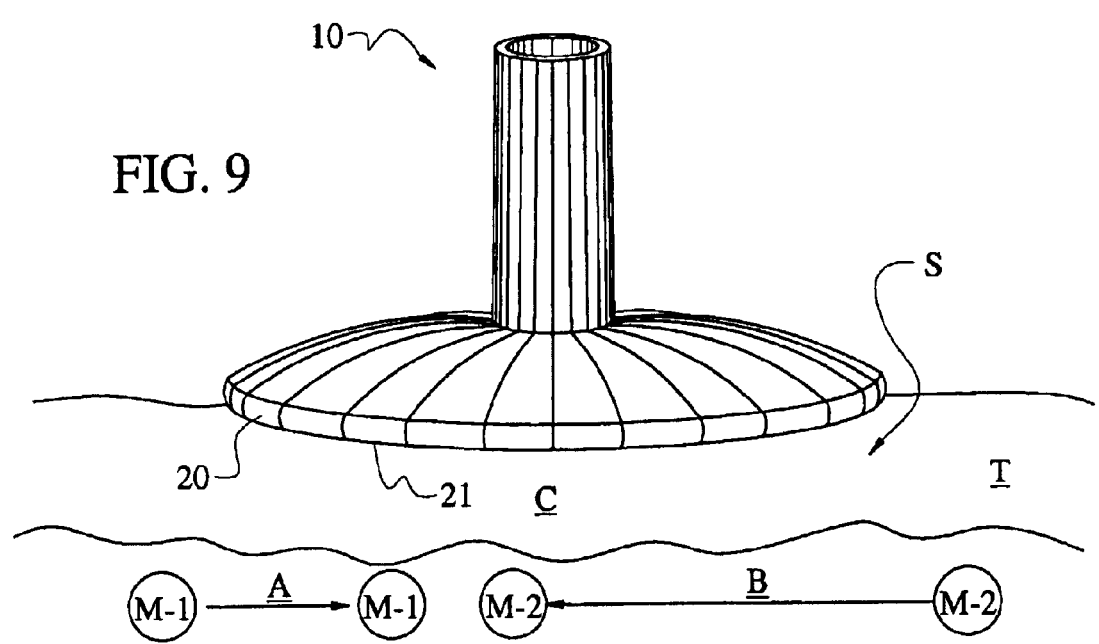
FIG. 9 illustrates the use of a nonpenetrating molecule manipulator to bring components of a multicomponent reactive system into opposition at a target site.

A first embodiment comprises a method for achieving an improved distribution and delivery of a desired molecule M into a target tissue T (FIG. 9). This method comprises the steps of placing at least one electrode with dual polarities or two electrodes having discrete polarities 20 generally adjacent but in nonpenetrating fashion to a surface of a target tissue T. A substance that includes the desired molecule M, such as a solution thereof, is introduced into the body systemically into an area near or on the target tissue T, either before or after the positioning of the device 10.

A first electrical potential is established between a pair of electrodes 20 and 21 that is sufficient to cause electromigration of the desired molecule M from an initial location to a more desirable location on the target tissue T. In a particular embodiment, the electric field strength range is 1–1500 V/cm in the microsecond to the millisecond range.

A second electrical potential is established between a pair of electrodes, which may or may not be the same poles on the multipolar electrode or pairs in the case of unitary polar members 20 and 21 as previously activated. The second potential is higher than the first electrical potential and is sufficient to cause electroporation in the target tissue T to enhance a movement of the desired molecule M into a cell. Exemplary field strengths and duration ranges include, but are not intended to be limited to, 1–10,000 V/cm in the nanosecond range to the millisecond range. In a particular embodiment the field strength range is 750–1500 V/cm over the microsecond to millisecond range. Either or both of the potentials can be delivered in a series of predetermined sequence of pulses, each of which can comprise pulses delivered sequentially or simultaneously.

A second method is for delivering a bioactive molecule to a subcutaneous target tissue T. This method comprises the steps of, as above, introducing a substance to containing the charged bioactive molecule M to a subcutaneous area adjacent the target tissue T. A device such as device 10 is placed generally adjacent but in nonpenetrating fashion to a target tissue T, and electrode pairs are again activated at a low and high level to achieve, respectively, an electromigration of the bioactive molecule M adjacent the target tissue T and an electroporation of a cell membrane within the target tissue T sufficient to permit entry of the bioactive molecule M into the cell interior.

A third method (FIG. 9) is for bringing two molecules M-1 into apposition at a desired target tissue site S for permitting a reaction therebetween, as in multicomponent labile systems, or a "cell bomb." This method comprises the steps of introducing a substance containing a first molecule M into a first area A adjacent the target tissue site S and introducing a substance containing a second molecule M-2 into a second area B adjacent the target tissue site S.

Next an electromigration of the first molecule M-1 and the second molecule M-2 is caused to a third area C that is actually within the target tissue site S. The electromigration is caused by at least a pair of electrodes placed against a surface generally adjacent but in nonpenetrating fashion to a target tissue. The third area C may actually comprise the first area A or the second area B, or another area distinct therefrom. The first molecule M-1 and the second molecule M-2 are then permitted to react at the third area C.

Another embodiment of a method of using one of the devices 10, 100, 110, or 120 comprises the step of introducing, such as by injection, although this is not intended as a limitation, a desired substance into the target tissue. The distal portions of the electrodes 68–72 are placed in contact with the tissue, and the sleeve 90, or the member 123 is moved to a position wherein the tissue area is closely encompassed by the electrodes 68–72, which ensures sufficient electrical contact therebetween. At least one, and preferably a plurality of, electrical pulses as desired are delivered to the electrodes 68–72 using the pulse generator 1, and thence to the tissue area for achieving electroporation and entrance of the desired substance into the target cells.

EXAMPLE

The methods of use of the nonpenetrating devices of the present invention are further described by the following example:

A nonpenetrating electrode device comprising four movable members attached to a support is used to deliver molecules to cells in vivo. This electrode is shown in FIG. 10 and comprises four straight-arm individual electrode members. The shaved left flank of C57B1/6 mice were treated with an injection of a 50 microliters volume of plasmid DNA coding for luciferase, a reporter molecule. After injecting the plasmid DNA, the electrode was placed against the skin in such a way that the electrically conductive tips surrounded the injection site. The sleeve 90 surrounding the members was moved from the proximal position to the distal end 80 of the device in order to close the conductive tips 80–83 into a rectangular configuration and to force contact between the skin and conductive portions of each member.

Electrical pulses were then applied between a set of two parallel electrodes and then to the other set of parallel electrodes.

The mice were then humanely euthanized 48 hours after treatment, and the treated skin was removed and analyzed for expression of luciferase, using standard laboratory methods as known in the art.

Table 1 shows the results of the experiment. The electrical field strength of the pulses was defined as the applied voltage divided by the distance between the electrodes (V/cm), and the time was the duration of each applied pulse.

TABLE 1

| Treatment Group | Number of Samples | Electrical Treatment | Mean Luciferase Expression |
|---|---|---|---|
| 1 | 4 | none | 1,123,344 |
| 2 | 4 | 1500 V/cm 100 µs | 1,735,343 |
| 3 | 4 | 1500 V/cm 100 µs, followed by 17 V/cm 100 ms | 7,046,177 |
| 4 | 4 | 1500 V/cm 100 µs, followed by 40 V/cm, 20 ms | 17,692,651 |

It is clear from Table 1 that the application of electric pulses to Treatment Groups 2–4 resulted in increased luciferase expression relative to the Control Group 1. These results also show that pulses of high field strength in combination with pulses of lower field strength can be used successfully to deliver molecules to a desired site.

Numerous other ways of practicing the invention described in this application are possible. These include, but are not limited to, using the described devices to cause: (1) electromigration, electroporation, and then electromigration again; (2) electromigration, followed by electroporation; (3) electroporation, followed by electromigration; (4) electroporation alone; (5) electromigration alone; (6) electromigration from a plurality of sides, either alone or (7) in combination with electroporation, either (8) before the electromigration or (9) after the electromigration or (10) simultaneously.

In addition, by using the instant devices as described it is possible to perform electromigration as well as electroporation using the same electrode members or, alternately, different electrode members. As known by those of ordinary skill in the art, the magnitude and duration of the electromagnetic fields is dependent on the particular combination of molecule(s) and tissue(s) under investigation; therefore, the electromagnetic field magnitudes and durations may be the same, similar, or different for inducing the migration of molecules and the electroporation of cells within tissues.

It may be appreciated by one skilled in the art that additional embodiments may be contemplated, including different electrode configurations adapted to provide high- and low-level fields foe causing electromigration and/or electroporation. In this application, a device being "configured" to produce an electromagnetic field in vivo means that (1) the portion of the device that comes in contact with body tissue or fluid is made of biocompatible materials; (2) the electrodes are capable of carrying the current required for electroporation and/or electromigration of living cells in vivo in an electrolyte that may include the tissue being treated, interstitial fluid, injected material at the treatment site, material applied to the target tissue, and combinations of the foregoing, and (3) the material between the electrodes which may be the same material as the support member, should have a sufficient dielectric constant so that it does not break down as a result of nearby electrodes being of opposite polarity during electrical treatment. Moreover, it will be apparent to those skilled in the art that where an electrode or system is configured to perform both electromigration and electroporation, such an electrode or system may be used to perform either or both functions.

It may be appreciated by one skilled in the art that additional embodiments may be contemplated, including alternate embodiments of the electrodes and nonpenetrating device.

In the foregoing description, certain terms have been used for brevity, clarity and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiments thereof, and the advantageous new and useful results obtained thereby, the new and useful constructions, and reasonable mechanical equivalents thereof obvious to those skilled in the art, are set forth in the appended claims.

What is claimed is:

1. A device for manipulating a molecule in vivo relative to a target tissue comprising:
    a support;
    at least four generally rectangular striplike electrode members having at least one conductive portion, the electrode members fixed to the support;
    the conductive portions are separated by nonconductive portions, each conductive portion being in circuit communication with an independently addressable respective portion of a source of electrical energy;
    at least two of the conductive portions positioned on different electrode members and locatable against a selected portion of the target tissue are configured to establish a first electromagnetic field between the at least two conductive portions sufficient to manipulate a molecule relative to a target tissue; and at least two of the conductive portions positioned on different electrode members and locatable against a selected portion of the target tissue are configured to establish a second electromagnetic field sufficient to cause transient permeability of a cell membrane within the target tissue.

2. The device recited in claim 1, further comprising means for delivering a preselected pattern of signals to selected conductive portions to effect a desired molecular result.

3. The device recited in claim 1, further comprising means for establishing at least two substantially different voltages approximately simultaneously on two or more conductive portions.

4. The device recited in claim 1, further comprising means to facilitate contact between the electrode member and the target tissue.

5. The device recited in claim 1, wherein each striplike electrode member is movable between a first position and a second position, wherein the electrode members are closer together than in the first position.

* * * * *